(12) United States Patent
Sáez Martinez et al.

(10) Patent No.: US 8,741,848 B2
(45) Date of Patent: Jun. 3, 2014

(54) PHARMACEUTICAL COMPOSITION OF MICROSPHERES FOR PREVENTING DIABETIC FOOT AMPUTATION

(75) Inventors: Vivian Maria Sáez Martinez, Ciudad de la Habana (CU); Rolando Páez Meireles, Ciudad de la Habana (CU); Jorge Amador Berlanga Acosta, Ciudad de la Habana (CU); Blas Yamir Betancourt Rodriguez, La Habana (CU); José Ángel Ramón Hernández, Camagüey (CU)

(73) Assignee: Centro de Ingenieria Genetica y Biotecnologia, Ciudad de la Habana (CU)

( * ) Notice: Subject to any disclaimer, the term of this patent is extended or adjusted under 35 U.S.C. 154(b) by 901 days.

(21) Appl. No.: 12/162,505

(22) PCT Filed: Jan. 29, 2007

(86) PCT No.: PCT/CU2007/000002
§ 371 (c)(1),
(2), (4) Date: Oct. 22, 2008

(87) PCT Pub. No.: WO2007/087759
PCT Pub. Date: Aug. 9, 2007

(65) Prior Publication Data
US 2009/0220608 A1    Sep. 3, 2009

(30) Foreign Application Priority Data
Jan. 31, 2006 (CU) .......................................... 21/06

(51) Int. Cl.
*A61K 38/00* (2006.01)

(52) U.S. Cl.
USPC .................................................. 514/18.6

(58) Field of Classification Search
None
See application file for complete search history.

(56) References Cited

U.S. PATENT DOCUMENTS

| 4,944,948 A | 7/1990 | Uster et al. |
| 5,100,669 A * | 3/1992 | Hyon et al. ............. 424/426 |

(Continued)

FOREIGN PATENT DOCUMENTS

| CN | 1720989 A | 1/2006 |
| EP | 0312208 A1 | 4/1989 |

(Continued)

OTHER PUBLICATIONS

Brown et al. Stimulation of healingof Chronic Wounds by EGF, Plastic and reconstructive surgery, vol. 88, No. 2, p. 189-194 (1988).*

(Continued)

*Primary Examiner* — Anand Desai
*Assistant Examiner* — Melissa Mercier
(74) *Attorney, Agent, or Firm* — Hoffmann & Baron, LLP

(57) ABSTRACT

The present invention relates to a pharmaceutical composition that comprises polymeric microspheres containing epidermal growth factor (EGF) for the application, by the parenteral route, into the lower limbs of diabetic patients with cutaneous chronic ischemic ulcerative wounds. The pharmaceutical composition described herein, in contrast with the state of the art, is useful because reduce the administration frequency during the treatment and allows for the healing of the ulcerative wounds in a shorter time interval with respect to the injection of equivalent quantities of non-encapsulated EGF.

5 Claims, 3 Drawing Sheets

(56) References Cited

U.S. PATENT DOCUMENTS

| | | | |
|---|---|---|---|
| 5,130,298 | A | 7/1992 | Cini et al. |
| 6,086,863 | A * | 7/2000 | Ritter et al. ............... 424/78.06 |
| 6,706,289 | B2 * | 3/2004 | Lewis et al. ................. 424/501 |
| 6,902,743 | B1 * | 6/2005 | Setterstrom et al. .......... 424/489 |
| 7,465,704 | B2 * | 12/2008 | Berlanga Acosta et al. ... 514/1.1 |
| 2005/0107294 | A1 | 5/2005 | Acosta et al. |
| 2008/0312139 | A1 | 12/2008 | Acosta et al. |
| 2009/0074850 | A1 | 3/2009 | Escalona et al. |

FOREIGN PATENT DOCUMENTS

| | | |
|---|---|---|
| EP | 0330180 A1 | 8/1989 |
| EP | 0451390 A1 | 10/1991 |
| EP | 0058481 A1 | 9/2008 |
| WO | WO9001331 A1 | 2/1990 |
| WO | WO9011781 A1 | 10/1990 |
| WO | WO9101719 A1 | 2/1991 |
| WO | WO03053458 A1 | 7/2003 |
| WO | WO03075949 A1 | 9/2003 |

OTHER PUBLICATIONS

Zhu et al., "Studies on Enhancing the Repair of Gangrenous Skin Diabetic Foot by Epidermal Growth Factor", Advances of Diabetes Mellitus in East Asia, No. 1141, p. 241-243 (1997).

Brown et al., "Stimulation of Healing of Chronic Wounds by Epidermal Growth Factor", Plastic and Reconstructive Surgery, vol. 88, No. 2, pp. 189-194 (1991).

Hogge et al., "The Potential Benefits of Advanced Therapeutic Modalities in the Treatment of Diabetic Foot Wounds", Journal of the American Podiatric Medical Assoc., vol. 90, No. 2, pp. 57-65 (2000).

Brown et al., "Enhancement of Epidermal Regeneration by Biosynthetic Epidermal Growth Factor", The Journal of Experimental Medicine, vol. 163, No. 5, pp. 1319-1324 (1986).

J. Lee, "Formulation Development of Epidermal Growth Factor", Die Pharmazie, 57:12, p. 787-790 (2002).

U.S. Appl. No. 12/159,159, Jun. 25, 2008.

U.S. Appl. No. 12/197,001, filed Aug. 22, 2008.

* cited by examiner

PHARMACEUTICAL COMPOSITION OF MICROSPHERES FOR PREVENTING DIABETIC FOOT AMPUTATION

This application is the U.S. National Phase of, and Applicants claim priority from, International Application Number PCT/CU2007/000002 filed 29 Jan. 2007 and Cuban Application bearing Serial No. CU 2006-0021 filed 31 Jan. 2006, which are incorporated herein by reference.

TECHNICAL FIELD

The present invention is related to a pharmaceutical composition that comprises polymeric microspheres containing epidermal growth factor (EGF) for the application, by the parenteral route, into the lower limbs of diabetic patients with cutaneous chronic ischemic ulcerative wounds for preventing diabetic limb amputation.

PREVIOUS ART

The Diabetes Mellitus is the main non-traumatic risk factor for the amputation of lower limbs. The ulceration of the foot is a significant complication of the Diabetes with an annual incidence slightly superior to 2% (Abbott C. A., et al (2002) The North-West Diabetes Foot Care Study: incidence of, and risk factors for, new diabetic foot ulceration in a community-based patient cohort. *Diabet. Med.* 19(5):377-84). At least 15% of diabetic patients develop chronic ulcers in their feet throughout their lifetimes (Reiber G. E. (1996) The epidemiology of diabetic foot problems. *Diabet. Med.* 13 Suppl 1:S6-11) and, approximately 10%-30% of these patients are estimated to require lower limb amputation (Lipsky B. A. (2004) Medical treatment of diabetic foot infections. *Clin. Infect. Dis.* 39 Suppl 2:S104-14). Mortality to the 5 years of the patients who suffered an amputation of lower limbs is about 50-60% (Reiber G. E. (1996) The epidemiology of diabetic foot problems. *Diabet. Med.* 13 Suppl 1:S6-11). Several methods have been used for the treatment of diabetic patients with cutaneous chronic ischemic ulcerative wounds. They include a rigorous metabolic control, prophylaxis of the modifiable risk factors, surgical debridements, use of dressings, antimicrobial treatment of the infections, elimination of the pressure of the injured area, use of skin grafts, growth factors and the use of revascularization methods in case of indication.

After the metabolic control, the surgical debridement is the most important treatment for the healing of the diabetic ulcer and should be carried out before any other local therapeutic modality. The surgical debridement consists of removing all dead and infected tissue (including bones) from the injured region, as well as the surrounding callous tissues.

The use of dressings for diabetic foot ulcers is well established, and although several kinds of dressings have been studied, the advantages of each kind of dressing over the others are not known. Besides, since studies on the use of dressings have been few, and they have been directed mainly to low-grade ulcers, more evidences from clinical trials are required to demonstrate their efficacy. New kinds of dressings, which have been studied in clinical trials, include those based on a semipermeable polymeric membrane, promogram (a collagen matrix), alginate, carboxymethylcellulose, hyaluronan and those that use sub-atmospheric pressure (Eldor R., et al. (2004) New and experimental approaches to treatment of diabetic foot ulcers: a comprehensive review of emerging treatment strategies. *Diabet Med.* 21(11):1161-73).

Several methods have been developed to create skin substitutes that are placed on the ulcer. For example, Dermagraft is produced by seeding fibroblasts of human dermis on a synthetic scaffold of bioabsorbible material. This device has shown to be effective in low-grade ulcers with a greater proportion of healing in a smaller time interval. (Marston W. A., et al. (2003) Dermagraft Diabetic Foot Ulcer Study Group. The efficacy and safety of Dermagraft in improving the healing of chronic diabetic foot ulcers: results of a prospective randomized trial. *Diabetes Care* 26:1701-5). The Apligraf consists of a layer of dermis composed of human fibroblasts in a matrix of bovine colagen type I and one epidermis layer formed by human keratinocytes. In a similar way, this substitute of skin has shown to produce a significantly greater and faster healing of injuries when it is applied in neuropathic low-grade and not infected ulcers (Veves A., et al (2001) Graftskin, a human skin equivalent, is effective in the management of non-infected neuropathic diabetic foot ulcers: a prospective randomized multicenter clinical trial. *Diabetes Care* 24:290-5).

In a phase III randomized, double-blind, placebo-controlled clinical trial, a gel formulation of Platelet Derived Growth Factor (PDGF) showed to be effective and safe for the treatment of diabetic patients who have neuropathic ulcers with good sanguineous perfusion (Wieman T. J., et al (1998) Clinical efficacy of beclapermin (rh PDGF-BB) gel. *Diabetes Care* 21 (5):822-7). Most of the patients (95%) included in this study have ulcers with an area $\leq 10$ cm$^2$ according to the evaluation by planimetry. Becaplermin gel 100 µg/g, in comparison with placebo, significantly increased the complete healing of the injuries in 43% (50 vs. 35%, p=0.007) and decreased the time required to achieve this effect in 32% (86 vs. 127 days, p=0.013). The satisfactory results with PDGF o becaplermin (Regranex) lead to their approval for the treatment of neuropathic ulcers located in the inferior members of diabetic patients, which extend until the subcutaneous tissue or more deeply and have a suitable sanguineous flow (Brem H., Sheehan P., Boulton A. J. (2004) Protocol for treatment of diabetic foot ulcers. *Am. J. Surg.* 187(5A):1S-10S).

Recently a method for the administration of a healing agent like Epidermal Growth Factor (EGF) was published, which consists of the infiltration of an EGF solution in the injury by means of several injections (WO 03/053458). But it has a clear disadvantage: it is very traumatic for the patient since the application of injections in the injury is extremely painful. In each treatment several injections must be applied and the patient must receive the treatment in alternating days during several weeks. Considering the disadvantages of this method, the use of a sustained release formulation of EGF could reduce the frequency of the drug administration, which would greatly enhance patient convenience and compliance.

There is a patent (U.S. Pat. No. 6,086,863) in which regulating and growth factors (i.e. Epidermal Growth Factor) can be included in prophylactic or therapeutic compositions containing microspheres of polystyrene or other non-degradable polymers, to improve the repair process of wounds such as diabetic foot ulcers, by means of the local application of a suspension of these microspheres in an appropriate vehicle. Topical application of drugs has the limitation related to the poor control of the dose that reaches the site of action since several factors can interfere with the drug absorption, among them the presence of necrotic tissue and local exudates, impairment of blood flow, enzymes that degrade the EGF can be mentioned.

Therefore, an important problem in the treatment of diabetic foot ulcers is to determine the effective dose of a drug that provokes the regeneration of the ischemic tissue and prevents the diabetic limb amputation.

Many other patents have focused on other methods designed for accelerating the healing rate. Nevertheless, none of these methods has proven to be widely effective.

DETAILED DESCRIPTION OF THE INVENTION

In general, the present invention refers to a pharmaceutical composition that contains microspheres loaded with Epidermal Growth Factor, to be administered by parenteral route in the lower limbs of diabetic patients who have cutaneous chronic ischemic wounds, with the objective of preventing the amputation of these members. In the present invention, the term microspheres includes microspheres and nanospheres.

The encapsulation of EGF in microspheres allows: (i) the slow release of the drug and (ii) protection of EGF against degradative processes such as the protein digestion by the proteases located in the site of action.

In this invention, the microspheres can be described like polymeric spheres with the drug homogeneously dispersed in all their volume, which is released in a controlled form.

In the context of this invention, the term "controlled release" includes the release of the drug in a continuous, discontinuous, linear or nonlinear form. This is accompanied by using different compositions from the polymeric matrix, inclusion of excipients that modify the release profiles and/or the addition of polymer degradation enhancers or other modifications, which made of individually or combined, produce the expected effect in the properties of the composition.

The microspheres are obtained by the double emulsion/solvent evaporation method as described by Okada et al. (U.S. Pat. No. 4,652,441).

The polymers preferred for the development of this invention are those that, by their properties, are biocompatibles and biodegradable. The last condition is of extreme importance since it allows the parenteral application of the formulation by its infiltration in the injury. Especially the homopolymers of glycolic or lactic acid and the copolymers derived from both poly (lactide-co-glycolide) (abbreviated PLGA) are preferred. These polymers possess characteristics that have turned them excellent biomateriales for the manufacture of sutures, fixation orthopedic devices and polymeric matrixes for drug delivery systems (Ashammakhi N., et al (2001) Developments in Craniomaxillofacial Surgery: Use of Self-Reinforced Bioabsorbable Osteofixation Devices. *Plast. Reconstr. Surg.* Special Topic: 167-80; Eppley B. L. (2005) Use of resorbable plates and screws in pediatric facial fractures. *J. Oral Maxillofac. Surg.* 63(3):385-91). Taking care of its properties, they are biocompatible and biodegradable; besides from offering the possibility of varying the release profiles of the drug based on the composition of the polymeric matrix, the molecular weight of the polymer and the addition of other excipients to the particles.

In addition to the PLGAs, other polymers with similar properties like biocompatibility and biodegradability, can be used. They include polycaprolactone, polyhydroxybutyrate-polyhydroxyvalerate copolymers, polylactic acid-polycaprolactone copolymers, polyorthoesters and polyanhydrides.

In a preferred embodiment, the microspheres of the pharmaceutical composition have a diameter that is in the rank between 1 and 100 µm and the EGF constitutes the 1.6-2.4% of the total mass of the microspheres.

In another preferred embodiment, the EGF encapsulated in the microspheres is released, after the first day of its infiltration, in amounts between 5 and 10 µg per day and it conserves their physical-chemical and biological properties during 14 days. Another aspect of the present invention refers to the treatment of ischemic injuries of a diabetic patient, through the administration by means of the local infiltration, in the local tissue that includes the edges and bottom of the injury, of the pharmaceutical composition above mentioned.

The microencapsulation of protein drugs requires special attention in relation to the activity of these biomolecules after the microencapsulation process. This is due to the fact that proteins are, in its majority, sensitive to high temperatures that frequently are generated in the encapsulation processes and to the organic solvent used for dissolving the polymers. On the other hand, each protein exhibits its own behavior in the microencapsulation processes. Considering these aspects, the establishment of a methodology for the preparation of microspheres loaded with proteins with their biological activity unchanged, requires of an exhaustive study in order to select the appropriated method, polymer, solvent, additives, etc.

As the active agent, the pharmaceutical composition can contain EGF obtained from natural sources, by means of chemical synthesis or by the recombinant DNA technology.

The pharmaceutical composition can also contain, as a part of the vehicle, some additional drugs of the following groups: antimicrobials (penicillins, cephalosporins, quinolone, metronidazole, clindamycin, vancomycin, macrolides, tetracyclins, aztreonam and imipenem), anesthetics, analgesics from the group of the non-steroidal anti-inflammatories, drugs with angiogenic action (vascular endothelial growth factor, fibroblast growth factor), other growth factors (granulocyte colony stimulating factor) or erythropoietin.

Cutaneous chronic ischemic ulcerative wound of lower limbs of diabetic patients is the pathology treated with the pharmaceutical composition that is the object of this invention. Depending on both: the conditions of the injury and the characteristics of the patient to be treated, the microspheres included in the pharmaceutical composition could require the coencapsulation of another molecule. These additional therapeutic agents belong to the group of antimicrobials, anesthetics, analgesics from the group of the non-steroidal anti-inflammatory drugs, drugs with angiogenic action, and other growth factors.

The pharmaceutical composition, previous to its administration to the patients, should be suspended in an appropriate vehicle, which can be either a saline solution containing viscosity enhancers such as carboxymethylcellulose, hydroxypropylmethylcellulose and detergents such as polysorbates or a thermosensitive hydrogel of the PEG-PLGA-PEG type or a derivative from chitosan or dextran.

The pharmaceutical composition object of this invention allowed reducing the administration frequency during the treatment and unexpectedly increased the therapeutic benefit by reducing the total time of the treatment, since the healing of the injuries was faster than that of injuries treated with equivalent amounts of non-encapsulated EGF. The improved therapeutic effect of our formulation was not expected, because the slow release profile achieved produces low EGF concentrations. Unexpectedly also, another formulation in which some excipients were used in order to accelerate the EGF release and thus to obtain greater concentrations of the drug did not have the therapeutic effects of the formulation of this invention.

EXAMPLES

In order to present a more complete description of the invention, the following examples are described:

Example 1

Figure 2:
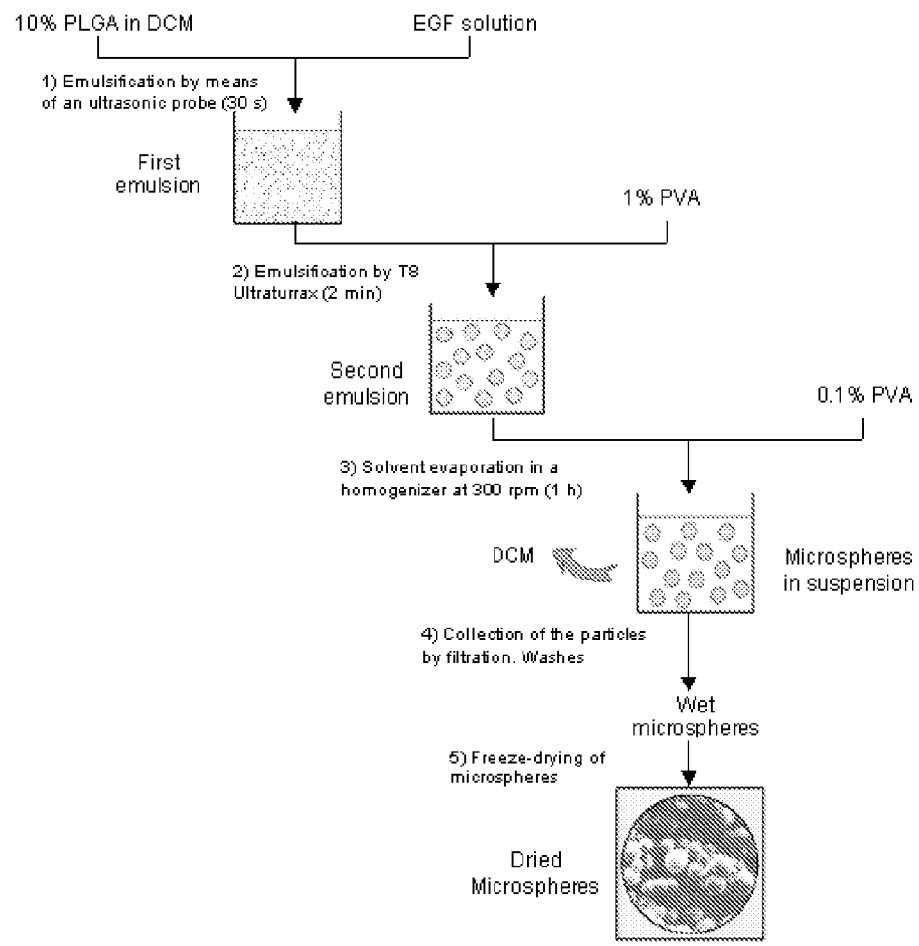
FIG. 2. Diagram of the process for obtaining the microspheres loaded with EGF by the double emulsion—solvent evaporation method.

Preparation of the Pharmaceutical Composition Containing PLGA Microspheres with EGF Preparation of the Microspheres Loaded with EGF Polymeric solution (PLGA 50:50 (Sigma, St. Louis, Mo., USA) 10% (w/v)) was prepared by dissolving 1 g of the polymer in dichloromethane (DCM). One milliliter of the PLGA solution was deposited in a glass container and 200 µl of an aqueous solution of EGF at 20 mg/ml was added. This mixture was sonicated during 30 seconds by means of an ultrasonic probe (IKASONIC U 200 S control (IKA Labortechnik, Germany). The first emulsion was added to 40 ml of 1% polyvinyl alcohol and the second emulsion was obtained by means of a vigorous agitation of the phases at 14 000 rpm using a T8 Ultraturrax (IKA Labortechnik, Germany). The double emulsion was added to 140 ml of 0.1% polyvinyl alcohol 30 000-70 000 (Sigma, St. Louis, Mo., USA) and stirred in a homogenizer (IKA Labortechnik, Germany) at 300 rpm during 1 h for evaporating dichloromethane. Finally, microspheres were collected by filtration, washed 5 times with 50 ml of distilled water and dried by freeze-drying in a lyophilizer (Edwards, UK). Dried microspheres was stored at 4° C. until they were used (FIG. 2).

The microspheres of EGF with excipientes were obtained following the same procedure but with the addition of Pluronic F-127 (10 mg) and NaCl (0.5 mg) in the internal aqueous phase.

Characterization of Microspheres Containing EGF

The efficiency of the microencapsulation process and protein loading of the particles were calculated, by means of the determination of EGF concentration by the microBCA assay, in the resulting solution from the digestion of particles with 1N NaOH which were neutralized with 1N HCl before the determination.

Figure 3:
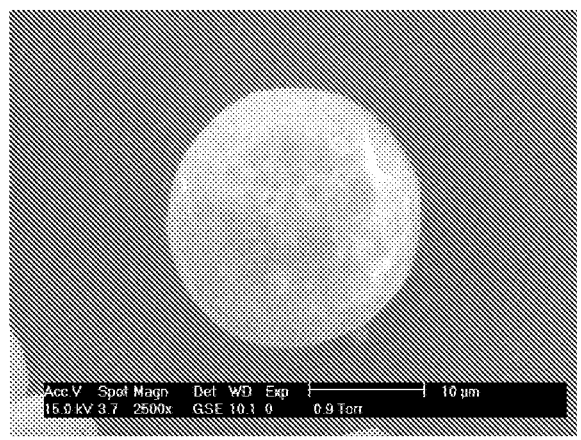
FIG. 3. Scanning electron micrograph of a microsphere loaded with EGF.

Microparticles of spherical form were obtained as a result from the microencapsulation process. They exhibited a regular surface and pores (FIG. 3). These microspheres were obtained with a yield of about 85%. It was possible to incorporate, in the microspheres, between the 40-60% of the total protein mass introduced in the encapsulation process. The particles exhibited a protein loading between 1.6 and 2.4%. The size of the microspheres was smaller than 25 µm.

TABLE 1

Characteristics of microspheres containing EGF.

| | Microspheres of EGF | Microspheres of EGF with F127 and NaCl |
|---|---|---|
| Yield (%) | 83 ± 2 | 83 ± 3 |
| Encapsulation efficiency (%) | 54 ± 3 | 48 ± 4 |
| Protein loading (%) | 1.98 ± 0.05 | 1.72 ± 0.06 |
| Particle size (µm) | 19 ± 3 | 24 ± 4 |

The inclusion of excipients did not vary, in a significant way, the characteristics of the microspheres containing EGF.

In Vitro Release of Encapsulated EGF

Fifty mg of microspheres loaded with EGF was suspended in 1 milliliter of receiving fluid (0.001% Tween 80 and 0.1% sodium azide, in PBS pH 7.2). The suspension was incubated at 37° C. under gentle stirring. At specified time intervals (0.25 (6 h), 0.5 (12 h), 1, 3, 7 and 14 days), samples were centrifuged for 5 min at 5000 rpm in a Hettich table centrifuge (Tuttlingen, Germany), the supernatant was collected and equal volume of fresh receiving fluid was added. The concentration of EGF in each withdrawn sample was assessed with the microBCA assay.

Figure 4:
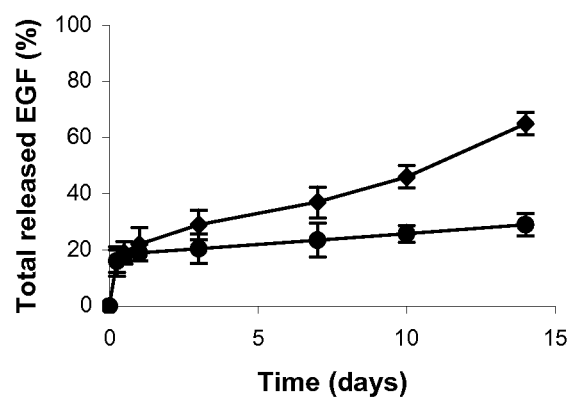
FIG. 4. Release profile of EGF from PLGA microspheres. The X-axis shows time in days and the Y-axis represents the quantity of EGF released which is expressed as a percent of the total EGF contained in the microspheres that were used in the experiment, (♦) fast release formulation and (●) slow release formulation.

The release profile of EGF encapsulated in the PLGA microspheres exhibited a burst release, which happened during the first day and another stage in which the EGF release occurs continuously during the following 14 days. Throughout the first stage approximately 20% of the total encapsulated protein was released in both preparations, whereas in the rest of the evaluation period the release profiles were different: liberation of EGF from microspheres with excipients reached almost 65% (in an approximated rate of 28 µg per day) and up to 30% was released from particles without excipients (in an approximated rate of 7 µg per day) (FIG. 4).

Characterization of EGF Released In Vitro

This experiment has the objective of demonstrating that the encapsulated EGF conserves their physical-chemical and biological properties. The properties of the EGF, released during the incubation period (14 days), were evaluated.

The EGF released during the first day, until the 7 and 14 days was characterized by means of several analytical techniques: reversed-phase high-performance liquid chromatography (RP-HPLC), slab-sodium dodecyl sulfate-polyacrylamide gel electrophoresis (SDS-PAGE), enzyme-linked immunosorbent assay (ELISA) and in vitro antiviral activity bioassay. The results appear in table 2.

TABLE 2

Physical-chemical and biological properties of EGF released in vitro.

| | EGF released | | | |
|---|---|---|---|---|
| Analysis | 1 days | 7 days | 14 days | Reference[d] |
| ELISA (%)[a] | 89 | 83 | 87 | 88 |
| SDS-PAGE (%)[b] | 98 | 100 | 99 | 100 |

TABLE 2-continued

Physical-chemical and biological properties of EGF released in vitro.

| Analysis | EGF released | | | Reference[d] |
|---|---|---|---|---|
| | 1 days | 7 days | 14 days | |
| RP-HPLC (%)[c] | 95 | 94 | 94 | 95 |
| Specific activity (UI/mg) | $7.0 \times 10^5$ | $7.1 \times 10^5$ | $6.8 \times 10^5$ | $7.2 \times 10^5$ |

[a] Percent of EGF that was immunorecognized with respect to the mass which was quantified by microBCA assay.
[b] Percent corresponding to the main band detected at 6000 Da.
[c] Percent corresponding to the main specie.
[d] EGF used to obtain the microspheres These results allow affirming that the released EGF has physical-chemical and biological characteristics similar to the EGF used to obtain the microspheres.

Figure 5:
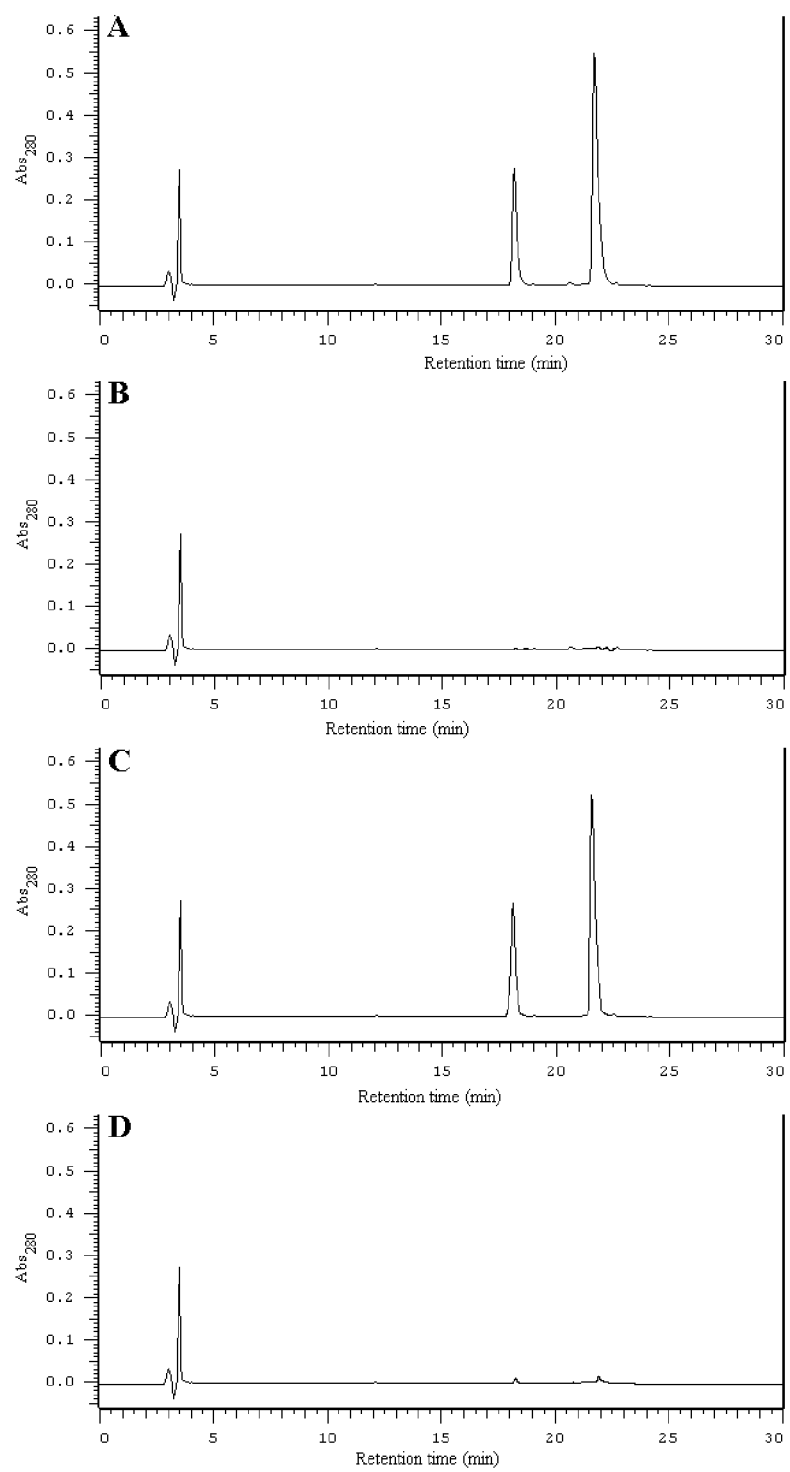
FIG. 5. Reverse-phase high-performance liquid chromatography of EGF digested with trypsin under different conditions. A: Control, B: Free EGF, C: EGF encapsulated in PLGA microspheres, D: EGF mixed with empty PLGA microspheres.

Effect of the Microencapsulation in the Stability of EGF Against to the Action of Proteases One mg of EGF was prepared independently in three different conditions: (i) dissolved in 1 ml of 4% sodium hydrogen carbonate ($NaHCO_3$), (ii) encapsulated in PLGA microspheres (2% in weight) and suspended in 1 ml of 4% $NaHCO_3$ and (iii) mixed with 50 mg of empty PLGA microspheres and suspended in 1 ml of 4% $NaHCO_3$. After that, 100 µl of 200 µg/ml trypsin in 4% $NaHCO_3$ was added to each preparation and they were incubated at 37° C. during 4 hours with gentle stirring. One mg of EGF dissolved in 1.1 ml of 4% $NaHCO_3$ was used as control. The reaction was stopped by adding 10 µl of trifluoracetic acid. Samples containing microspheres were centrifuged during 10 minutes at 6000 g and supernatant was separated from the pellet. The EGF microencapsulated or adsorbed on the microspheres was separated from the polymer by an extraction with dichloromethane/acetic acid (Ruiz J. M., et al (1989) Microencapsulation peptide: a study of the phase separation of poly (D,L-lactic acid-co-glycolic acid) copolymers 50/50 by silicone oil. *J. Pham. Sci.* 49:69-77). All the samples were analyzed by RP-HPLC following the procedure described by Han et al. (Han K., et al. (1998) Site-specific degradation and transport of recombinant human epidermal growth factor (rhEGF) in the rat gastrointestinal mucosa. *Int. J. Pharm.* 168:189-197). The results (FIG. 5) show that both non-encapsulated EGF and the EGF mixed with empty microspheres was completely degraded. However, the encapsulated EGF was protected against the proteolysis and its chromatographic profile was similar to the one of the control.

Example 2

In Vivo Effect (in Animal Model) of Encapsulated EGF Versus Free EGF

Experimental Model of Controlled Acute Injuries

The experiment described here was made with the objective of evaluating the healing effect, in acute injuries of satisfactory prognosis, of the new pharmaceutical formulation with microspheres of EGF to be used for infiltration or parenterally, by means of injections in the wound edges and bottom.

Experimental Biomodel:

Male Wistar rats with a body weight of 225-250 grams. Animals were maintained in controlled areas of the animal facility at CIGB under a constant illumination schedule of 12×12 hours, air change cycles, and free access to the diet. The rats were individually housed into T3 boxes with replacement of the bedding (previously sterilized) every 48 hours.

Induction of Ulcers:

Animals were anesthetized by intraperitoneal injection of ketamine/xylazine. The back of rats comprising the area from the retroscapular space up to the sacrum was mechanically and chemically depilated. This region was aseptisized with a solution of povidone-iodine and isopropyl alcohol. The area over the skin selected for the induction of ulcers was marked with Chinese ink in order to create circular, total width lesions with the aid of 9 mm-diameter biotomes (AcuDrem, µl, USA).

Figure 1:
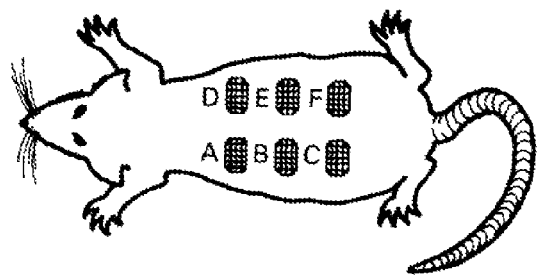
FIG. 1. Scheme that represents the location of the ulcers induced in the animal model.

As indicated in FIG. 1, six symmetric and equidistant injuries were induced in each animal. Injuries were washed with a sterile saline solution and their inner border was delineated with permanent ink for later calculation of wound area at time zero. The lesions of all animals were hygienized daily with 70% ethanol and sterile saline solution before the application of any treatment.

Experimental Groups:

The ulcers created in the animals were randomly assigned to the following experimental treatment groups by using an input order/group cross-matching table:

Group I—no treatment. It is a control for the spontaneous evolution.

Group II—placebo (vehicle used to suspend the microspheres: 0.3% carboximethylcellulose, 0.1% Tween20 and 0.9% sodium chloride which is locally infiltrated).

Group III—infiltration of microspheres (without excipients) containing 675 micrograms of EGF, which was suspended in 1 ml of the vehicle designed for this formulation. Infiltrations were performed on the wound edges and bottom.

Group IV—infiltration of microspheres (with excipients) containing 675 micrograms of EGF, which was suspended in 1 ml of the vehicle designed for this formulation. Infiltrations were performed on the wound edges and bottom.

Group V—Free EGF (75 mg/ml) in 0.9% saline solution.

Each group consisted of 10 rats; therefore 60 wounds per group were studied. Treatments were performed daily, in animals treated with the formulations without microspheres, inserting the needle (27½) on the edges and bottom of injuries. Prior to each treatment animals were sedated with diazepam by the intra-peritoneal route. Animals treated with vehicle or formulations containing microspheres loaded with EGF, were infiltrated only once.

Determination of the Level of Wound Closure. Histological Processing:

The injuries were traced on transparent sheets for calculating the kinetics of the wounds contraction over the following times: Time 0—represents 100% of opened injury area and 0% wound contraction, Time 1—72 hours after the induction of injuries, Time 2—five days after the induction of injuries, Time 3—seven days after the induction of injuries, Time 4—nine days after the induction of injuries. The ninth day was set as the end of this study, on which the animals were sacrificed, according to previous experiences on the kinetics of the spontaneous healing of these lesions. The images with the borders of injuries were digitized. The area of injuries and the percent of contraction were calculated by using the image analysis software DIGIPAT. Statistical analysis of each parameter were performed with the SPSS package by using the non-parametric Mann Whitney U test, a signification level of $p<0.05$ was assumed.

Animals were sacrificed by intra-peritoneal injection with an overdose of sodium pentobarbital (250 mg/kg). Injuries were dried up from the panniculus carnosus and fixed in 10% neutral formalin for later inclusion in paraffin. The hematoxylin/eosin, van Giesson's and Masson's trichromic stains were used. For each group, the number of animals with 100% epithelization of the injury, and with a stratified and differentiated epidermis was determined.

The values for the kinetic of wound contraction are shown in Table 3 (contraction values in mm are expressed in terms of percent change of wound size with respect to wound size at Time 0).

TABLE 3

Values of ulcer contraction.

Contraction kinetic of controlled acute ulcers (%)

| Group | Time 0 | Time 1 | Time 2 | Time 3 | Time 4 |
|---|---|---|---|---|---|
| Group I | 0 | 6.1 ± 2.1 | 9.3 ± 2.2 | 37.6 ± 3.3 | 56.7 ± 3.8 |
| Group II | 0 | 8.3 ± 2.2 | 11.4 ± 2.4 | 41.5 ± 2.7 | 67.4 ± 4.5 |
| Group III | 0 | 11.4 ± 3.3* | 22.5 ± 3.8* | 69.8 ± 4.8* | 86.8 ± 3.5* |
| Group IV | 0 | 9.9 ± 1.1 | 12.8 ± 1.4 | 52.4 ± 3.1 | 69.6 ± 4.9 |
| Group V | 0 | 9.6 ± 1.2 | 11.6 ± 1.5 | 51.5 ± 2.7 | 67.4 ± 4.5 |

*This means a statistical difference of $p < 0.05$ with respect to the other groups. Mann Whitney U test.

Unexpectedly, the formulation that contains microspheres of EGF with slower release profile (without co-encapsulated excipients), exerted the most powerful of the effects of contraction of the wounds edges, which, in other words, means that it exerts the most favorable effect in the acceleration of the total healing. The contraction represents the convergence of several consolidated events that approximate the wound to the remodeling phase.

In Table 4 appears the percent of area occupied by mature and organized granulation tissue of the ulcers in each experimental group. The calculations were made on the collected samples in Time 4 quantifying the number of positive microscopic fields coincidentally with the van Giesson's and Masson's trichromic reactions in each sample. Two pathologists made the evaluations independently and in a blind form.

TABLE 4

Percent of granulated area at Time 4 for each experimental group.

| | Area covered by mature granulation tissue (%) |
|---|---|
| Group I | 48.7 ± 5.7 |
| Group II | 62.4 ± 3.9 |
| Group III | 84.5 ± 4.3 |
| Group IV | 64.7 ± 2.7 |
| Group V | 61.3 ± 2.6 |

Sixty wounds per experimental group were studied by means of positive reactions to collagen fibers.

Unexpectedly, the formulation based on microspheres of EGF with slower release profile (without coencapsulated excipients) exerted the most powerful of the effects on the process of establishment and maturation of the granulation tissue, which corresponds with the description above mentioned for the process of wounds contraction.

The effect of the treatments was also studied in relation to the epithelialization process of the injuries. The microscopic aspect of epithelium was evaluated considering the re-epithelialization of the ulcer, the presence of stratified epithelium, and the existence of a total keratin layer. For the microscopic study a central longitudinal hemisection was practiced to the injuries and the resultant pieces were included in the same paraffin block. A total of 120 histological cuts by experimental group were studied, which represent 60 injuries. The results are expressed in Table 5.

TABLE 5

Effect of the treatments on epithelialization of wounds.

| | No. of wounds 100% epithelialization | No. of wounds with a mature epithelium |
|---|---|---|
| Group I | 32 | 28 |
| Group II | 56 | 45 |
| Group III | 81* | 73* |
| Grupo IV | 64 | 56 |
| Group V | 60 | 51 |

*This means a statistical difference of $p < 0.05$ with respect to the other groups. Mann Whitney U test Group III, treated with the formulation based on microspheres of EGF of slow release profile (without coencapsulated excipientes), surprising showed the best indicators of epithelial answer, supported by the total re-epithelialization and the maturity of epithelium.

Experimental Model of Chronic Cutaneous Ulcers

The following experiment was aimed at evaluating the healing effect, in chronic lesions of poor prognosis that simulate lesions in diabetic patients, of the new pharmaceutical formulation that is based on microspheres containing EGF, to be used for infiltration.

Experimental Biomodel:

Male Wistar rats with a body weight of 225-250 grams. Animals were maintained in controlled areas of the animal facility at CIGB under a constant illumination schedule of 12×12 hours, air change cycles, and free access to the diet. The rats were individually housed into T3 boxes with replacement of the bedding (previously sterilized) every 48 hours. The animals had previously been treated for two months with a 0.01% methylglyoxal solution to create a glycosylation environment similar to that occurring in a diabetic patient of long term evolution. Among other organic damages, this leads to a slow down of the granulation and remodelation of wounds (Berlanga J., Cibrian D., et al. (2005) Methylglyoxal administration induces diabetes-like microvascular changes and perturbs the healing process of cutaneous wounds. *Clin Sci (Lond)*. 109(1):83-95).

Induction of Ulcers:

Animals were anesthetized by intraperitoneal injection of ketamine/xylazine. The back of rats comprising the area from the retroscapular space up to the sacrum was mechanically and chemically depilated. This region was aseptisized with a solution of povidone-iodine and isopropyl alcohol. The area over the skin selected for the induction of ulcers was marked with Chinese ink in order to induce circular, total width lesions with the aid of 9 mm-diameter biotomes (AcuDrem, μl, USA). Six symmetric and equidistant injuries were induced in each animal. Injuries were washed with a sterile saline solution and their inner border was delineated with permanent ink for later calculation of wound area at time zero. The injuries of all animals were hygienized daily with 70% ethanol and sterile saline solution before the application of any treatment.

Experimental Groups:

The ulcers created in the animals were randomly assigned to the following experimental treatment groups by using an input order/group cross-matching table:

Group I—no treatment. It is a control for the spontaneous evolution.

Group II—placebo (vehicle used to suspend the microspheres: 0.3% carboximethylcellulose, 0.1% Tween20 and 0.9% sodium chloride which is locally infiltrated).

Group III—infiltration of microspheres (without excipients) containing 1 mg of EGF, which was suspended in 1 ml of the vehicle designed for this formulation. Infiltrations were performed on the wound edges and bottom.

Group IV—infiltration of microspheres (with excipients) containing 1 mg of EGF, which was suspended in 1 ml of the vehicle designed for this formulation. Infiltrations were performed on the wound edges and bottom.

Group V—Free EGF (75 mg/ml) in 0.9% saline solution.

Each group consisted of 10 rats; therefore 60 wounds per group were studied. Treatments were performed daily, in animals treated with the formulations without microspheres. Prior to each treatment animals were sedated with diazepam by the intra-peritoneal route. Animals treated with vehicle or formulations containing microspheres loaded with EGF, were infiltrated only once.

Determination of the Level of Wound Closure. Histologic Processing:

The injuries were traced on transparent sheets for calculating the kinetics of the wounds contraction over the following times: Time 0—represents 100% of opened injury area and 0% wound contraction, Time 1—72 hours after the induction of injuries, Time 2—five days after the induction of injuries, Time 3—seven days after the induction of injuries, Time 4—nine days after the induction of injuries and Time 5—fourteen days after the induction of injuries. The fourteenth day was set as the end of this study, on which the animals were sacrificed, according to previous experiences on the kinetics of the spontaneous healing of these lesions. The images with the borders of injuries were digitized. The area of injuries and the percent of contraction were calculated by using the image analysis software DIGIPAT. Statistical analysis of each parameter were performed with the SPSS package by using the non-parametric Mann Whitney U test, a signification level of $p<0.05$ was assumed.

Animals were sacrificed by intra-peritoneal injection with an overdose of sodium pentobarbital (250 mg/kg). Injuries were dried up from the panniculus carnosus and fixed in 10% neutral formalin for later inclusion in paraffin. The hematoxylin/eosin, van Giesson's and Masson's trichromic stains were used. For each group, the number of animals with 100% epithelization of the injury, and with a stratified and differentiated epidermis was determined.

The values for the kinetic of wound contraction are shown in Table 6.

TABLE 6

Contraction kinetic values of wounds during the evaluation period.

| Group | Contraction kinetic of chronic ulcers (%) | | | | |
|---|---|---|---|---|---|
| | Time 1 | Time 2 | Time 3 | Time 4 | Time 5 |
| Group I | 3.18 ± 1.1 | 5.31 ± 1.15 | 15.8 ± 1.37 | 21.8 ± 1.54 | 40.82 ± 4.41 |
| Group II | 4.14 ± 2.2 | 7.63 ± 1.12 | 17.3 ± 1.81 | 23.81 ± 1.53 | 39.75 ± 3.63 |
| Group III | 6.55 ± 1.14* | 25.33 ± 4.1** | 35 ± 3.51** | 43.15 ± 3.66** | 67.2 ± 3.44** |
| Group IV | 6.25 ± 1.5 | 17.3 ± 1.51 | 19.7 ± 2.1 | 29.9 ± 2.85 | 48.16 ± 3.14 |
| Group V | 6.67 ± 1.8 | 15.4 ± 1.63 | 16.8 ± 3.8 | 28.1 ± 3.31 | 45.72 ± 3.55 |

*This means a statistical difference of $p < 0.05$ with respect to the other groups.
**This means a statistical difference of $p < 0.01$ with respect to the other groups. Mann Whitney U test.

Contraction values in mm are expressed in terms of percent change of wound size with respect to wound size at Time 0.

Unexpectedly, the formulation that contains microspheres of FCE with slower release profile (without co-encapsulated excipients), exerted the most powerful of the effects of contraction of the wounds edges, which, in other words, means that it exerts the most favorable effect in the acceleration of the total healing. The contraction represents the convergence of several consolidated events that approximate the wound to the remodeling phase. It is remarkable that these wounds simulate the biochemical microenvironment of the diabetic wound in which the contraction mechanism is pathologically abolished in a partial or total form.

In Table 7 appears the percent of area occupied by mature and organized granulation tissue of the chronic ulcers in each experimental group. The calculations were made on the collected samples in Time 5 quantifying the number of positive microscopic fields coincidentally with the van Giesson's and Masson's trichromic reactions in each sample. Several pathologists and a consultant made the evaluations independently and in a blind form.

TABLE 7

Percent of granulated area at Time 5 for each experimental group.

| | Area covered by mature granulation tissue (%) |
|---|---|
| Group I | 31.78 ± 3.25 |
| Group II | 29.85 ± 2.28 |
| Group III | 81.6 ± 3.55** |

TABLE 7-continued

Percent of granulated area at Time 5 for each experimental group.

|  | Area covered by mature granulation tissue (%) |
|---|---|
| Group IV | 68.12 ± 2.55 |
| Group V | 65.72 ± 2.98 |

Sixty wounds per experimental group were studied by means of positive reactions to collagen fibers.
\**This means a statistical difference of $p < 0.01$ with respect to the other groups. Mann Whitney U test Unexpectedly, the formulation based on microspheres of EGF with slower release profile (without coencapsulated excipients) exerted the most powerful of the effects on the process of establishment and maturation of the granulation tissue, which corresponds with the description above mentioned for the process of wounds contraction.

The effect of the treatments was also studied in relation to the epithelialization process of the injuries. The microscopic aspect of epithelium was evaluated considering the re-epithelialization of the chronic ulcer, the presence of stratified epithelium, and the existence of a keratin layer. For the microscopic study a central longitudinal hemisection was practiced to the injuries and the resultant pieces were included in the same paraffin block. A total of 120 histological cuts by experimental group were studied, which represent 60 injuries. No injury was eliminated by bacterial contamination. The results are expressed in Table 8.

TABLE 8

Effect of the treatments on epithelialization of chronic ulcers.

|  | No. of wounds with 100% of epithelialization | No. of wounds with a mature epithelium |
|---|---|---|
| Group I | 18 | 13 |
| Group II | 16 | 12 |
| Group III | 74 | 69 |
| Group IV | 62 | 44 |
| Group V | 59 | 42 |

Group III, treated with the formulation based on microspheres of EGF having a slow profile (without excipients), surprising showed the best indicators of epithelial answer, supported by the total re-epithelialization and the maturity of epithelium.

Example 3

In Vivo Effect (in Patients with Cutaneous Chronic Ischemic Ulcerative Wounds) of Encapsulated EGF Vs Free EGF The formulation based on microspheres of EGF of slow profile (without excipients) was administered in patients with diabetic foot ulcers and risk of major amputation. A diabetic female patient of 58 years of age with a chronic ulcer, in the right foot, of an area of 30.5 $cm^2$ and evidences of ischemia of the affected member was treated with the formulation object of the present invention. After injury debridement, the formulation with microspheres of EGF with slower release profile was administered, once every 15 days during a month by means of infiltration of the wound edges and bottom. The fast formation of useful granulation tissue was observed since the first week after the treatment start, reaching to cover 100% of the affected area by the third week. The patient showed a satisfactory evolution with complete closing of the injury and avoiding the need to indicate amputation. The pharmaceutical composition was well tolerated and no adverse effects were detected.

The perilesional and intralesional administration of this formulation favored the formation of granulation tissue and the wound closure, which unexpectedly promoted the ulcer healing process to occur in a shorter time interval with respect to previous treatments and the need of amputation was avoided. This modality of treatment turned out to have better tolerance by virtue of the substantial reduction of the injections.

The invention claimed is:

1. A method for treating diabetic foot ulcers or cutaneous chronic ischemic wounds of the lower limbs of diabetic patients and to prevent the amputation of said limbs, said method comprising administering a pharmaceutical composition comprising Epidermal Growth Factor (EGF) encapsulated in poly(lactide-co-glycolide) (PLGA) microspheres by means of local infiltration by injection to the edges and bottom of said ulcers or wounds, wherein the EGF has a release rate after day 1 of administration between 5 and 10 μg/day for 14 consecutive days.

2. The method of claim 1, wherein said microspheres have a diameter in the range of 1 μm to 100 μm.

3. The method of claim 1, wherein the EGF constitutes 1.6-2.4% of the total mass of the microspheres.

4. The method of claim 1, wherein the EGF conserves its physical-chemical and biological properties.

5. The method of claim 1, wherein the microspheres are suspended in a thermosensitive PEG-PLGA-PEG hydrogel.

* * * * *

UNITED STATES PATENT AND TRADEMARK OFFICE
CERTIFICATE OF CORRECTION

PATENT NO. : 8,741,848 B2
APPLICATION NO. : 12/162505
DATED : June 3, 2014
INVENTOR(S) : Vivian Maria Sáez Martinez et al.

Page 1 of 1

It is certified that error appears in the above-identified patent and that said Letters Patent is hereby corrected as shown below:

IN THE SPECIFICATION:

Column 8, Line 11; Column 11, Line 10

Now Reads: "(AcuDrem, µl,"
Should Read: "(AcuDrem, Fl,"

Signed and Sealed this
Ninth Day of September, 2014

Michelle K. Lee
*Deputy Director of the United States Patent and Trademark Office*